United States Patent
Stroppolo et al.

(10) Patent No.: US 10,245,284 B2
(45) Date of Patent: Apr. 2, 2019

(54) GRANULAR COMPOSITION FOR ORAL ADMINISTRATION

(71) Applicant: ALPEX PHARMA S.A., Mezzovico (CH)

(72) Inventors: Federico Stroppolo, Aldesago (CH); Gabriele Granata, Leggiuno (IT)

(73) Assignee: ALPEX PHARMA S.A., Mezzovico (CH)

( * ) Notice: Subject to any disclaimer, the term of this patent is extended or adjusted under 35 U.S.C. 154(b) by 0 days.

(21) Appl. No.: 14/829,912

(22) Filed: Aug. 19, 2015

(65) Prior Publication Data
US 2017/0049806 A1 Feb. 23, 2017

(51) Int. Cl.
*A61K 31/785* (2006.01)
*A61K 47/02* (2006.01)
*A61K 9/00* (2006.01)
*A61K 9/14* (2006.01)

(52) U.S. Cl.
CPC .......... *A61K 31/785* (2013.01); *A61K 9/0095* (2013.01); *A61K 9/143* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 4,172,120 A | 10/1979 | Todd et al. | |
| 4,439,419 A | 3/1984 | Vecchio | |
| 4,902,501 A | 2/1990 | Bandi et al. | |
| 5,496,545 A | 3/1996 | Holmes-Farley et al. | |
| 5,607,669 A | 3/1997 | Mandeville et al. | |
| 2002/0155091 A1 | 10/2002 | Huval et al. | |
| 2003/0219400 A1 | 11/2003 | Shoemaker et al. | |
| 2011/0189121 A1 | 8/2011 | Genth | |
| 2016/0030345 A1 * | 2/2016 | Lee | A61K 31/192 514/576 |

FOREIGN PATENT DOCUMENTS

| | | |
|---|---|---|
| CN | 101757627 A | 6/2010 |
| CN | 103385854 A | 11/2013 |
| EP | 2591768 A1 | 5/2013 |
| GB | 1181003 | 2/1970 |
| WO | 9007343 A1 | 7/1990 |
| WO | 0040224 A1 | 7/2000 |
| WO | 2005065291 A2 | 7/2005 |
| WO | 2006050314 A2 | 5/2006 |
| WO | 2006072054 A1 | 7/2006 |
| WO | WO 2013185789 A1 * 12/2013 ........... A61K 9/0056 |
| WO | 2016135065 A1 | 9/2016 |

OTHER PUBLICATIONS

Summary of Product Characteristics of Renagel 400 mg film-coated tablets.
"SYLOID® 244 FP Silica: Silica Excipient for Pharmaceutical Applications", Grace Davison Discovery Sciences, 2009, XP-002762040, 2 pages.
Database WPI, "Use of thiazolidinedione insulin sensitizer and bile acid sequestrant in preparing drug for treating diabetes, diabetes complications and diseases associated with diabetes", Thomson Scientific, 2010, Week 201702 , XP002762038, 2 pages.
Database WPI, "Pharmaceutical composition used for treating overactive bladder, comprises oxybutynin, oil phase, e.g. mineral oil, surfactant, e.g. sodium dodecyl sulfate, and proppant, e.g. hydroxypropyl methylcellulose", Thomson Scientific, 2014, Week 201420, XP002762039, 4 pages.
International Search Report and Written Opinion for International Application No. PCT/EP2016/068022 (17 Pages) (dated Oct. 5, 2016).

* cited by examiner

*Primary Examiner* — Dennis J Parad
(74) *Attorney, Agent, or Firm* — Lucas & Mercanti, LLP

(57) ABSTRACT

The present invention relates to a granular composition for oral suspension characterized by the presence of an insoluble resin and a silica gel.

7 Claims, No Drawings

GRANULAR COMPOSITION FOR ORAL ADMINISTRATION

FIELD OF THE INVENTION

The present invention relates to a granular composition for oral suspension characterized by the presence of an insoluble resin and a silica gel.

BACKGROUND OF THE INVENTION

It is known that insoluble resins, such as Sevelamer, Cholestyramine or Colesevelam, are extremely helpful in treating several pathologies such as hypercholesterolemia (acting as bile acid sequestrants) or hyperphosphataemia (acting as phosphate binding drug) in patients with chronic kidney diseases.

These insoluble resins are all characterized by:
elevated molecular weight;
low or very low solubility, or insolubility;
elevated therapeutically dosage to be administered;
elevated electrostatic charge;
low flowability.

These characteristics cause serious issues in formulating granular compositions for oral suspension to be filled in a container, such as sachets or cans.

In fact, due to these negative properties, the Health Authorities (such as the Food and Drug Administration) did not authorize to fill containers (sachets or cans) with said insoluble resins over the limits of ±5% of the target weight for each container.

Usually, in order to solve the difficulties related to the low flowability of the granular composition and to the poor uniformity content of the containers, the formulators are obliged to use special dosage equipments.

However, the use of special dosage equipments often do not solve these problems because of the poor wettability and floating on the surface of the liquid—thus remaining immiscible—of the granular composition, caused by the electrostatic charges of said granular composition.

Thus, granular compositions for oral administration comprising such insoluble resins in higher amount for each container and with better flowability and uniformity are needed.

Silica gels are usually used in several industrial applications, and particularly in pharmaceutical field, because of their considerable absorbing power, and their enormous surface area.

Surprisingly, it has been found that the granular compositions comprising insoluble resins, such as Sevelamer, Cholestyramine or Colesevelam, lose all the negative characteristics mentioned-above when a certain amount of silica gel, preferably highly porous silica gel having a mesoporous structure such as Syloid® XDP or Syloid® FP, is added to said granular compositions, thus allowing a better wettability of the insoluble granular composition, and the preparation of reliable dosage forms. In addition, if such silica gels are used in the compositions of the present invention an higher amount of insoluble resins for each container can be used.

SUMMARY OF THE INVENTION

The present invention refers to a granular composition for oral suspension characterized by the presence of an insoluble resin and a silica gel.

DETAILED DESCRIPTION OF THE INVENTION

For the purpose of the present invention, the expression "porosity of a material" refers to the % ratio between the volume of the pores and the total volume of the considered material.

For the purpose of the present invention, the expression "highly porous material" refers to a material which has a porosity higher than 20%, preferably higher than 40%, even more preferably higher than 60%. In a preferred embodiment, the highly porous material has a porosity comprised in the range of 60-95%.

For the purpose of the present invention the expression "mesoporous material" refers to a material with a porous diameter size comprised in the range of 2-50 nm.

Silica gels (such as Syloid®), which are characterized by a high porosity and a mesoporous structure, are widely used within the pharmaceutical industry as excipients and processing aids.

The properties and the characteristics of such silica gels are known in the literature. They are referenced by FDA's as inactive ingredients and are specifically cited in numerous drug patents due to their unique morphology and properties that improve the handling, adsorption, and dissolution of many pharmaceuticals. In fact, the combined adsorption capacity, porosity, particle size, and greater internal surface area allow them to provide several benefits simultaneously that can help to minimize the number of excipients required, to expedite manufacturing, and to improve efficacy of the final dosage form.

Examples of commercial Syloid® to be used according to the present invention are Syloid® XDP-3050, Syloid® XDP-3150, and Syloid® FP.

Syloid® XDP usually refers to silica carriers consisting of an optimized mesoporous material, engineered for transforming liquids to free flowing solids, particularly oily actives and lipid-based systems. Generally speaking, such carriers lead to several advantages, such as transforming liquids to easy to handle solids, improving bioavailability of oily actives, increasing API loading in solid dosage forms; quick releasing of API.

Syloid® FP are usually used in the pharmaceutical applications as effective desiccants to increase the stability of moisture-sensitive APIs, as efficient conditioners for powder formulations used in suspensions, as capillary wetting agents for better release and disintegration.

The present invention refers to a granular composition for oral administration comprising a non soluble resin and a silica gel selected from the group consisting of: Syloid® FP and Syloid® XDP. More preferably, the silica gel is Syloid® XDP. Even more preferably, Syloid® XDP is Syloid® XDP-3050 or Syloid® XDP-3150. Syloid® XDP-3050 is preferred.

Preferably, the silica gel is Syloid® FP in the range of 0.1%-5% (w/w)

Preferably, the silica gel is Syloid® XDP in the range of 0.4%-1.0% (w/w).

Preferably, the insoluble resin of the granular composition of the present invention is selected from the group consisting of: Sevelamer carbonate, Sevelamer hydrochloride, Cholestyramine and Colesevelam hydrochloride. Sevelamer carbonate is preferred.

In a preferred embodiment, the granular composition of the present invention, further comprises a flavour, when the insoluble resin is Sevelamer carbonate.

More preferably, the flavour is selected from the group consisting of: citrus flavour, berry flavour, peach flavour, apricot flavour, mint flavour, anise flavour, grape flavour, cherry flavour and a mixture thereof. Citrus flavour is preferred.

Preferably, the granular composition of the present invention further comprises an artificial sweetener when citrus flavor is used. Preferably the artificial sweetener is aspartame.

Surprisingly, it has been found that the silica gel disclosed in the present invention advantageously reduces the electrostatic charges of the granular composition; therefore, the wettability of the insoluble granular composition is increased, thus allowing the preparation of reliable dosage forms. In fact, by using the silica gel disclosed herein the dispersion in a liquid, when orally administered, is facilitated.

In addition, another advantage of the present invention is that the granular composition here disclosed can be easily filled in sachets using a traditional dosing machine filled by gravity, and not the special equipments usually used and known in the state of the art, thus producing sachets with a Variation Coefficient (CV) of no more than (NMT) 3% or filled in cans with CV of NMT 3%.

Moreover, when bulk in water, the granular composition of the present invention rapidly forms a jelly suspension, thus advantageously allowing the correct administration of the medicament.

The following examples better illustrate the present invention without limiting it.

Please note that, for the purposes of the present invention, the meaning of the following acronyms is reported below:

"CV" refers to "Variation Coefficient";

"PASS" refers to "Comply with the specifications";

"MT" refers to "More Than";

"TYPICAL" means that the flavour and taste are typical of the selected flavour.

Example 1

The following compositions A-S have been prepared by pouring the ingredients listed in the Tables below:

|  | A | | B | | C | | D | | E | | F | |
|---|---|---|---|---|---|---|---|---|---|---|---|---|
|  | mg | % | mg | % | mg | % | mg | % | mg | % | mg | % |
| Sevelamer carbonate | 2400.00 | 93.31 | 2400.00 | 93.31 | 2400.00 | 93.13 | 2400 | 92.73 | 2400 | 91.50 | 2400 | 93.31 |
| *Citrus* flavour | 66.60 | 2.54 | 66.60 | 2.54 | 66.60 | 2.58 | 66.66 | 2.57 | 66.60 | 2.54 | 66.60 | 2.54 |
| Propylen glycol alginate | 60.00 | 2.32 | 60.00 | 2.32 | 60.00 | 2.33 | 60.00 | 2.32 | 60.00 | 2.29 | 60.00 | 2.32 |
| NaCl | 40.00 | 1.54 | 40.00 | 1.54 | 40.00 | 1.55 | 40.00 | 1.55 | 40.00 | 1.52 | 40.00 | 1.54 |
| Syloid XDP-3050 | 23.40 | 0.91 | — | — | — | — | 2.30 | 0.10 | 128.60 | 5 | — | — |
| Syloid XDP-3150 | — | — | — | — | — | — | — | — | — | — | 23.40 | 0.91 |
| Aerosil V200 | — | — | 23.40 | 0.91 | — | — | — | — | — | — | — | — |
| Sucralose | 10.00 | 0.38 | 10.00 | 0.38 | 10.00 | 0.39 | 10 | 0.39 | 10.00 | 0.38 | 10.00 | 0.38 |
| Total | 2600 | 100 | 2600 | 100 | 2577 | 100 | 2579 | 100 | 2705 | 100 | 2600 | 100 |

|  | G | | H | | I | | L | | M | |
|---|---|---|---|---|---|---|---|---|---|---|
|  | mg | % | mg | % | mg | % | mg | % | mg | % |
| Cholestyramine | 4000 | 70.17 | 4000 | 70.17 | 4000 | 70.17 | 4000 | 70.17 | 4000 | 70.17 |
| Propylen glycol alginate | 250 | 4.39 | 250 | 4.39 | 250 | 4.39 | 250 | 4.39 | 250 | 4.39 |
| Fructose | 1255 | 22.02 | 1255 | 22.02 | 1300 | 22.81 | 1294 | 22.41 | 1045 | 21.23 |
| *Citrus* Flavour | 80 | 1.40 | 80 | 1.40 | 80 | 1.40 | 80 | 1.40 | 80 | 1.40 |
| Citric acid | 50 | 0.88 | 50 | 0.88 | 50 | 0.88 | 50 | 0.88 | 50 | 0.88 |
| Syloid XDP-3050 | 45 | 0.79 | — | — | — | — | 6 | 0.10 | 285 | 5.00 |
| Syloid XDP-3150 | — | — | — | — | — | — | — | — | — | — |
| Aerosil V200 | — | — | 45 | 0.79 | — | — | — | — | — | — |
| Aspartame | 20 | 0.35 | 20 | 0.35 | 20 | 0.35 | 20 | 0.35 | 20 | 0.35 |
| Total | 5700 | 100 | 5700 | 100 | 5700 | 100 | 5700 | 100 | 5700 | 100 |

|  | N | | O | | P | | Q | | R | | S | |
|---|---|---|---|---|---|---|---|---|---|---|---|---|
|  | mg | % | mg | % | mg | % | mg | % | mg | % | mg | % |
| Cholestyramine | 4000 | 44.44 | 4000 | 44.44 | 4000 | 44.44 | 4000 | 44.44 | 4000 | 44.44 | 4000 | 44.44 |
| Propylen glycol alginate | 90 | 1.00 | 90 | 1.00 | 90 | 1.00 | 90 | 1.00 | 90 | 1.00 | 90 | 1.00 |
| Saccharose | 4640 | 51.55 | 4640 | 51.55 | 4685 | 52.06 | 4676 | 51.80 | 4235 | 47.05 | 4640 | 51.55 |
| *Citrus* Flavour | 180 | 2.00 | 180 | 2.00 | 180 | 2.00 | 180 | 2.00 | 180 | 2.00 | 180 | 2.00 |
| Citric acid | 45 | 0.50 | 45 | 0.50 | 45 | 0.50 | 45 | 0.50 | 45 | 0.50 | 45 | 0.50 |
| Syloid XDP- | 45 | 0.50 | — | — | — | — | 9.00 | 0.10 | 450 | 5.00 | — | — |

-continued

| | | | | | | | | | | | | |
|---|---|---|---|---|---|---|---|---|---|---|---|---|
| 3050 Syloid XDP-3150 | — | — | — | — | — | — | — | — | — | — | 45 | 0.5 |
| Aerosil V200 | — | — | 45 | 0.50 | — | — | — | — | — | — | — | — |
| Total | 9000 | 100 | 9000 | 100 | 9000 | 100 | 9000 | 100 | 9000 | 100 | 9000 | 100 |

The resulting mix were blended for 10 minutes and were collected in a container.

The mix were then characterized from physical point of view.

Physical characteristics of the mix

| Composition | Flowability | Bulk density [g/ml] | Tapped density [g/ml] | Appearance |
|---|---|---|---|---|
| A | 33.7° | 0.6 | 0.7 | Yellowish powder |
| B | Not measurable | 0.4 | 0.7 | Yellowish powder |
| C | Not measurable | 0.4 | 0.7 | Yellowish powder |
| D | 36.5° | 0.6 | 0.7 | Yellowish powder |
| E | 32.8° | 0.6 | 0.7 | Yellowish powder |
| F | 33.6° | 0.6 | 0.7 | Yellowish powder |
| G | 34.3° | 0.7 | 0.9 | Almost white powder |
| H | Not measurable | 0.6 | 0.9 | Almost white powder |
| I | Not measurable | 0.4 | 0.7 | Yellowish powder |
| L | 37.5° | 0.7 | 0.9 | Almost white powder |
| M | 32.5° | 0.7 | 0.9 | Almost white powder |
| N | 31.2° | 0.8 | 0.9 | Almost white powder |
| O | 42.0° | 0.8 | 1.0 | Almost white powder |
| P | Not workable flowability | 0.7 | 0.9 | Almost white powder |
| Q | 34.6° | 0.7 | 0.9 | Almost white powder |
| R | 30.5° | 0.7 | 0.9 | Almost white powder |
| S | 31.2° | 0.8 | 0.9 | Almost white powder |

The mix was then filled in a Marchesini RC 600 filling machine equipped with a dosing device filled by gravity, and the product was filled in Aluminium-Aluminium sachets in reason of 9.0 g each, or alternatively in a composite can, containing 239.4 or 378 g of granular and dispensed with a spoon corresponding to 5.7 g or 9.0 g of mixture.

Physical characteristics of the sachet/mix

| | Mean weight [mg] | CV [%] | Tightness of sachets |
|---|---|---|---|
| A | 2600 | ±2.5 | PASS |
| B | Not fillable | NA | NA |
| C | Not fillable | NA | NA |
| D | 2588 | ±10 | PASS |
| E | 2705 | ±2.5 | PASS |
| F | 2600 | ±2.5 | PASS |
| G | 5700 | ±2.5 | PASS |
| H | Not fillable | NA | NA |
| I | Not fillable | NA | NA |
| L | 5700 | 10 | PASS |
| M | 5700 | ±2.5 | PASS |
| N | 9000 | ±2.5 | PASS |
| O | 9000 | ±10 | PASS |
| P | 9000 | ±10 | PASS |
| Q | 9000 | ±2.5 | PASS |
| R | 9000 | ±2.5 | PASS |
| S | 9000 | ±2.5 | PASS |

A sachet comprising formula selected among A-S was then suspended in 60 ml of tap water; the characteristics of the derived suspensions are reported in the Table below

Characteristics of the suspension

| | Time of residence on the top of the suspension/water | Appearance of the suspension after 1 minute | Appearance of the suspension after 5 minutes | Taste of the suspension |
|---|---|---|---|---|
| A | 20" | Homogeneous, cloudy | Slightly precipitated | Typical of flavor |
| B | MT 10' | Product floating on the surface of water | Product floating on the surface of water | Typical of flavor and sandy |
| C | MT 10' | Product floating on the surface of water | Product floating on the surface of water | Typical of flavor c and sandy |
| D | 50" | Homogeneous, cloudy | Almost precipitated | Typical of flavor |
| E | 20" | Totally sediment | Totally sediment | Typical of flavor |
| F | MT10" | Homogeneous, cloudy | Slightly precipitated | Typical of flavor |
| G | 10" | Homogeneous, cloudy | Slightly precipitated | Typical of flavor |
| H | MT 10' | Product floating on the surface of water | Product floating on the surface of water | Typical of flavor and sandy |
| I | MT 10" | Product floating on the surface of water | Product floating on the surface of water | Typical of flavor and sandy |
| L | 20" | Homogeneous, cloudy | Almost sedimented | Typical of flavor |
| M | 10" | Totally sediment | Totally sediment | Typical of flavor |
| N | 10" | Homogeneous, cloudy | Slightly precipitated | Typical of flavor |
| O | 40" | Slightly precipitated | Almost precipitated | Typical of flavor |
| P | 40" | Slightly precipitated | Almost precipitated | Typical of flavor |
| Q | 20" | Homogeneous, cloudy | Slightly sedimented | Typical of flavor |
| R | MT 10' | Product floating on the surface of water | Products floating on the surface of water | Typical of flavor |
| S | 10" | Homogeneous, cloudy | Slightly precipitated | Typical of flavor |

From the data reported above, it is thus clear that both Syloid® XDP-3050 and Syloid® XDP-3150 are suitable for the present invention; Syloid® XDP-3050 is preferred.

By making a comparison between the suspensions comprising the following compositions:
A and B,
G and H, and
N and O;
where in compositions A, G and N Syloid® XDP-3050 has been used, and in compositions B, H and O AerosilV200 has been used, the suspension comprising Syloid® XDP-3050 showed an homogeneous and cloudy appearance after 1 minute, whereas in the suspensions comprising a silica gel different from Syloid® XDP-3050 the product floated on the surface of the water already after 1 minute. A similar result has been obtained for the suspensions where no silica gel is added to the compositions. In fact, for the compositions C, I and P, already after 1 minute the product floated on the surface of water, thus causing the problems in formulating granular compositions for oral suspension to be filled in a container mentioned above. The use of Siloyd® XDP-3050 advantageously overcomes these issues.

Moreover, a significant increase of Syloid® XDP-3050 (around 5%) in the composition, did not improve the physical parameters, but increased the sedimentation speed (see the compositions A and E, G and M, and N and R, where the appearance of the suspension after 1 minute of compositions A, G and N is "Homogeneous, cloudy", whereas for compositions E, M and R is "Totally sediment" or "Product floating on the surface of the water").

What is claimed is:

1. A granular composition in the form of an oral suspension in water comprising
   a non soluble resin selected from the group consisting of Sevelamer carbonate, Sevelamer hydrochloride, and Cholestyramine, and
   a highly porous silica gel having a mesoporous structure, wherein the highly porous silica gel is in the range of 0.1%-5% (w/w).

2. The granular composition according to claim 1, wherein the highly porous silica gel is in the range of 0.4%-1.0% (w/w).

3. The granular composition according to claim 1, wherein the non soluble resin is Sevelamer carbonate, and wherein said granular composition further comprises a flavor.

4. The granular composition according to claim 3, wherein the flavor is selected from the group consisting of: citrus flavor, berry flavor, peach flavor, apricot flavor, mint flavor, anise flavor, grape flavor, cherry flavor and a mixture thereof.

5. The granular composition according to claim 3, wherein the flavor is citrus flavor, and wherein the granular composition further comprises an artificial sweetener.

6. The granular composition according to claim 5, wherein the artificial sweetener is aspartame.

7. The granular composition according to claim 5, wherein the artificial sweetener is sucralose.

* * * * *